(12) United States Patent
Kudo

(10) Patent No.: US 11,369,259 B2
(45) Date of Patent: Jun. 28, 2022

(54) ENDOSCOPIC DEVICE AND HEAT RADIATOR

(71) Applicant: Olympus Corporation, Hachioji (JP)

(72) Inventor: Toshisato Kudo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 582 days.

(21) Appl. No.: 16/359,617

(22) Filed: Mar. 20, 2019

(65) Prior Publication Data

US 2019/0298162 A1 Oct. 3, 2019

(30) Foreign Application Priority Data

Mar. 30, 2018 (JP) .............................. JP2018-068584

(51) Int. Cl.
| | |
|---|---|
| A61B 1/00 | (2006.01) |
| A61B 1/06 | (2006.01) |
| G02B 23/24 | (2006.01) |
| G02B 23/26 | (2006.01) |
| A61B 18/12 | (2006.01) |

(52) U.S. Cl.
CPC ........ A61B 1/0676 (2013.01); A61B 1/00133 (2013.01); G02B 23/2476 (2013.01); G02B 23/26 (2013.01); A61B 1/00066 (2013.01); A61B 18/1206 (2013.01)

(58) Field of Classification Search
CPC .............. A61B 1/0676; A61B 1/00133; A61B 1/00066; A61B 18/1206; A61B 1/0661; A61B 1/128; G02B 23/2476; G02B 23/26; G02B 7/008; G02B 23/2469; H05K 7/20154; H05K 7/20436; H05K 2007/20081; F21V 29/83

USPC ......................................................... 600/160
See application file for complete search history.

(56) References Cited

U.S. PATENT DOCUMENTS

| | | | |
|---|---|---|---|
| 2009/0109429 A1* | 4/2009 | Scott .................... | G01N 29/043 356/237.1 |
| 2011/0034773 A1* | 2/2011 | Ishigami ............ | A61B 1/00128 600/160 |
| 2015/0055297 A1* | 2/2015 | Chilek ............... | H05K 7/20436 361/697 |

FOREIGN PATENT DOCUMENTS

| | | |
|---|---|---|
| JP | H02-034993 A | 2/1990 |
| JP | 5519211 | 4/2014 |
| JP | 2015-043084 A | 3/2015 |
| JP | 2017-169983 | 9/2017 |

OTHER PUBLICATIONS

Japanese Office Action dated Oct. 26, 2021 received in 2018-068584.

* cited by examiner

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscopic device includes a manipulator body and an insertion portion including opposed respective proximal and distal ends. The insertion portion is connected to the manipulator body via the proximal end. A first heat generator is configured to be attached to the manipulator body. A heat radiator is configured to be detachably attached to the manipulator body and is thermally connected to the first heat generator. The heat radiator includes at least one air inlet port through which air flows in and at least one air outlet port having an area smaller than an area of the at least one air inlet port.

17 Claims, 13 Drawing Sheets

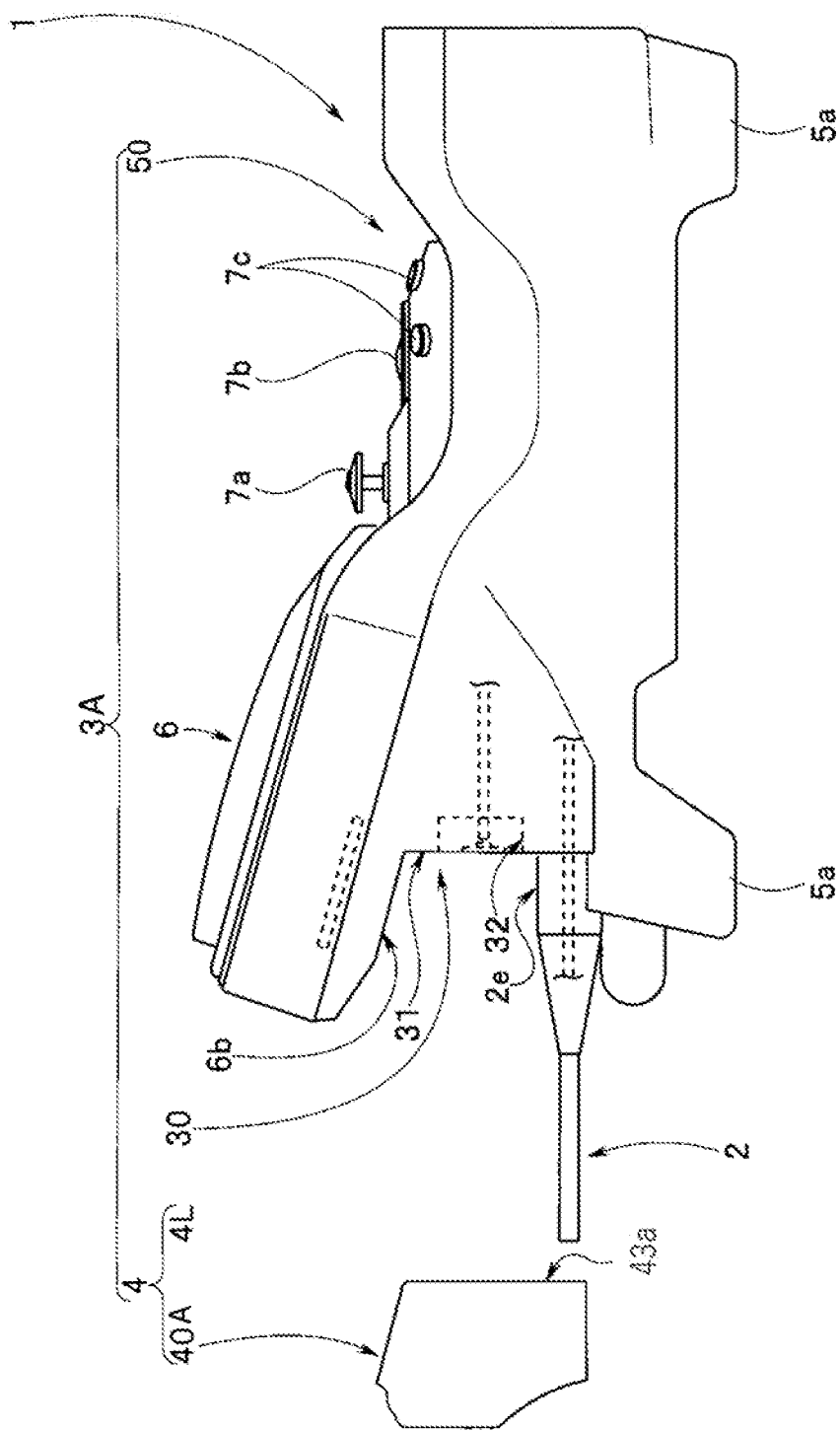

ENDOSCOPIC DEVICE AND HEAT RADIATOR

CROSS-REFERENCE TO RELATED APPLICATION

This application is a Non-provisional application which claim priority to the Japanese Patent Application No. 2018-068584 filed in the Japan Patent Office on Mar. 30, 2018, which is hereby incorporated by reference in its entirety.

TECHNICAL FIELD

The disclosed technology relates to an endoscopic device that has a heat generator in a gripper and also to a heat radiator for radiating the heat of a heat generator.

DESCRIPTION OF THE RELATED ART

Endoscopic devices are widely used in the industrial field and the medical field. When in use in the industrial field, for example, an endoscopic device is inserted into a thin and long part of a boiler, a turbine, an engine, or the like. Then, the endoscopic device produces an endoscopic image of a target region in the part. The user observes the endoscopic image that is displayed on a display device to determine whether or not there is a fault, a corrosion, or the like in the target region.

Recent years have seen light-emitting elements for use as endoscopic light sources. When a light-emitting element as an endoscopic light source is energized, it generates heat. The generated heat is conducted to a casing, gradually increasing the temperature of the casing. The casing whose temperature has been increased makes it difficult for the user to carry out observations for a long period of time. Japanese Patent No. 5519211 discloses an endoscopic device that has a main body that can be gripped by the user and that is easy to handle.

The disclosed endoscopic device includes a light source having a light-emitting element as a heat generating member and a light guide connected to the light-emitting element. The endoscopic device also includes a heat radiator thermally connected to the light source. The heat radiator has a portion extending into an outer housing and thermally connected to the light-emitting element.

The heat radiator has a plurality of first fins and a plurality of disk-shaped second fins that are exposed outwardly. The heat radiator functions as a heat sink that radiates outwardly the heat generated by the light-emitting element. At least part of the heat radiator that is heated to high temperatures is covered with a shield for preventing the user from contacting the heat radiator. The shield has a through hole defined in a ceiling thereof for ambient air to flow therethrough.

BRIEF SUMMARY OF EMBODIMENTS

However, the heat radiating capability of the heat radiator is likely to be reduced by the shield that covers part of the heat radiator. If the heat radiator is increased in size for a higher heat radiating capability, then the endoscopic device tends to become heavier, possibly impairing its portability.

The disclosed technology has been made in view of the above problems. It is an object of the disclosed technology to provide an endoscopic device that is lightweight and allows the user to carry out satisfactory observations for a long period of time with a small-size heat radiator that has an increased heat radiating capability with respect to a casing.

An endoscopic device according to an aspect of the disclosed technology includes an insertion portion, a casing connected to a proximal end of the insertion portion and functionable as a gripper, a first heat generator disposed in the casing for supplying illuminating light to a light guide, and a heat radiator disposed in the casing and thermally connected to the first heat generator, in which the heat radiator has an air inlet through which air flows in and an air outlet having an area smaller than an inlet area of the air inlet.

A heat radiator according to another aspect of the disclosed technology includes a plurality of heat radiating spaces, a plurality of air inlets which are disposed respectively in the heat radiating spaces and through which ambient air flows in, and an air outlet that has an area smaller than the air inlet and through which air flows out of the heat radiating spaces.

According to the disclosed technology, there is provided an endoscopic device that is lightweight and allows the user to carry out satisfactory observations for a long period of time with a small-size heat radiator that has an increased heat radiating capability with respect to a casing.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 10A is a view illustrating an endoscopic device having a manipulator body in which a heat radiator and a light source are integral with each other;

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Preferred embodiments of the disclosed technology will hereinafter be described below with reference to the drawings.

In each of the figures used in the description that follows, some of the components are drawn to different scales in order to illustrate themselves in sizes large enough to be recognized in the figures. The disclosed technology should not be limited to the numbers, shapes, size proportions, and relative positional relationships of the components depicted in the figures.

Figure 1:
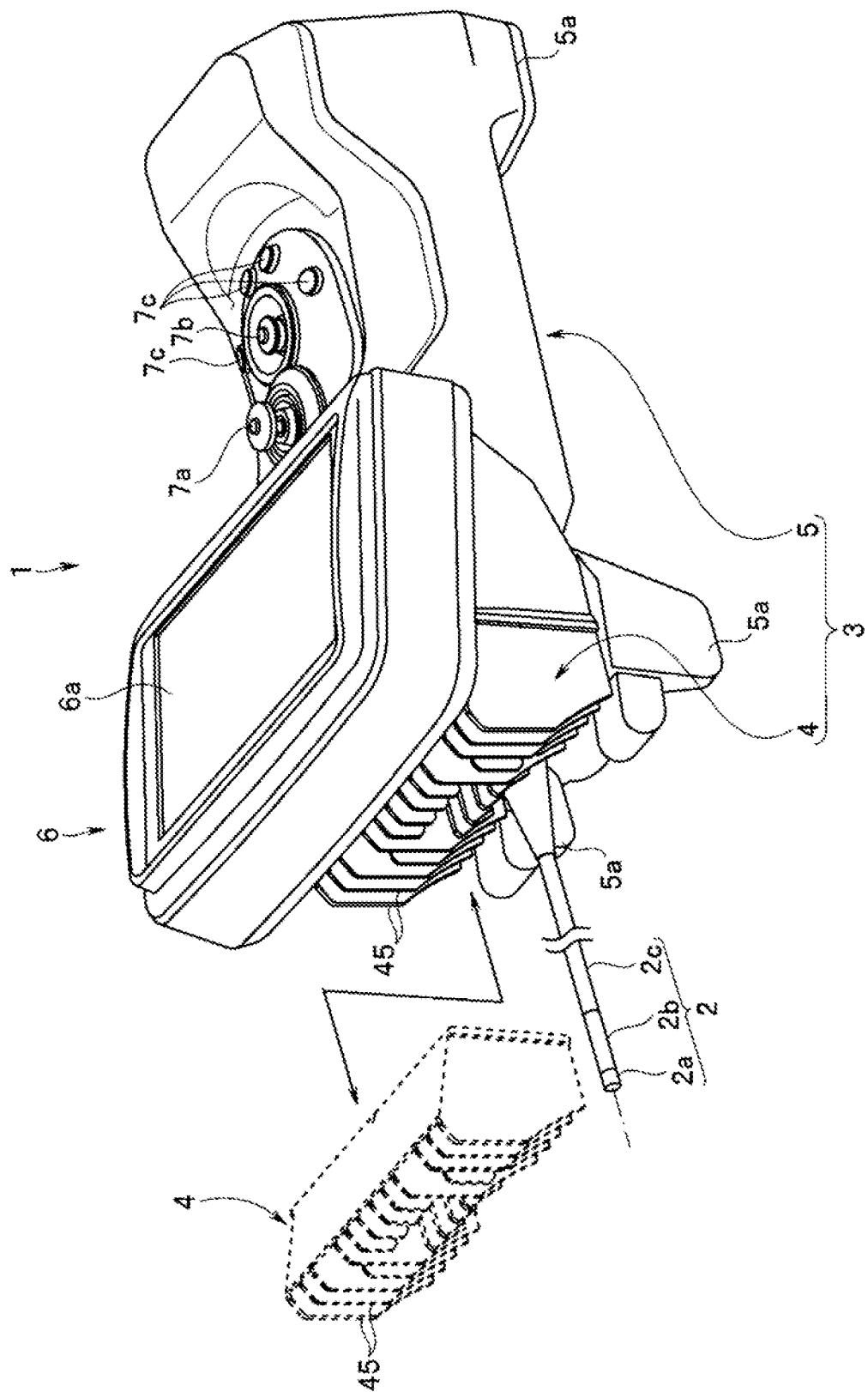
FIG. 1 is a view illustrating an endoscopic device.

An endoscopic device 1 illustrated in FIG. 1 is used in the industrial field, for example. The endoscopic device 1 has an insertion portion 2 that can be inserted into a part to be examined, such as a gas turbine, a pipe, etc., in an electric power station, for example.

Figure 2:
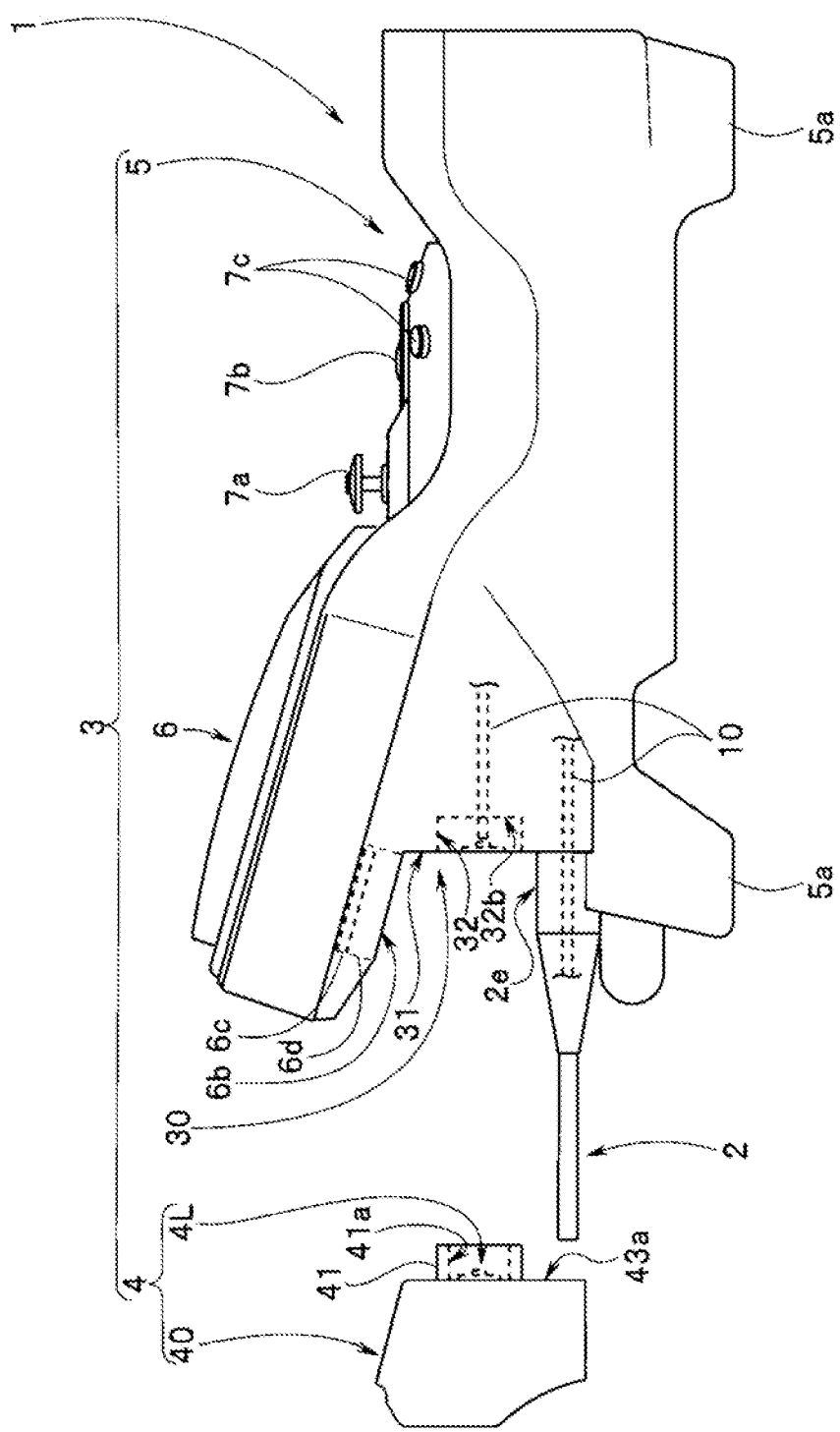
FIG. 2 is a view illustrating the endoscopic device where a light source unit of a manipulator is detached from a manipulator body.

The insertion portion 2 has a proximal-end side attached to a manipulator 3. The manipulator 3 includes a light source unit 4. The manipulator 3 has a manipulator body 5 as a casing substantially in the shape of a rectangular parallelepiped. The light source unit 4 is detachably attached to the manipulator body 5 as indicated by the broken lines. The light source unit 4 includes a light source 4L as a first heat generator, as illustrated in FIG. 2.

The insertion portion 2 is flexible and is of a tubular shape. The insertion portion 2 includes a proximal end portion 2a, a bendable portion 2b, and a flexible tube portion 2c that are joined together successively from a proximal end side thereof. The bendable portion 2b includes a plurality of bendable elements, not depicted, that are joined together, for example. According to the present embodiment, the bendable portion 2b is actively bendable in all directions around an insertion axis, including upward, downward, leftward, and rightward directions.

The upward, downward, leftward, and rightward directions are defined for the sake of convenience in accordance with the upward, downward, leftward, and rightward directions of an image captured by an image capturing device, for example.

The manipulator body 5 has a function as a gripper. When the user grips the manipulator body 5, the user can grip the manipulator 3 while carrying out observations.

Legs 5a project from a lower surface of the manipulator body 5. When the legs 5a are placed on a desktop or the like, the user can carry out observations without gripping the manipulator body 5.

The manipulator 3 can change its posture depending on the manner in which it is gripped. For the sake of brevity, however, the directions of the manipulator 3 are defined for convenience as follows: One of the longitudinal directions of the manipulator 3 toward an end thereof is defined as a proximal end direction, the other longitudinal direction toward the other end as a proximal-end direction, and four directions perpendicular to the longitudinal axis of the manipulator 3 respectively as upward, downward, leftward, and rightward directions.

As illustrated in FIGS. 1 and 2, a display unit 6 substantially in the shape of a flat rectangular parallelepiped is integrally mounted on an upper portion of the proximal end side of the manipulator body 5. The display unit 6 includes a display 6a such as a Liquid Crystal Display (LCD) or the like on its upper surface. The display unit 6 is slanted at a predetermined angle with respect to the longitudinal directions of the manipulator body 5 for increasing the visibility of the display 6a.

A display unit rear surface, denoted by 6b in FIG. 2, is similarly slanted at the predetermined angle. The display unit 6 also includes a video processing circuit board (hereinafter referred to as "circuit board") 6c as a second heat generator. The display unit 6 further includes a heat radiating plate 6d as a cooled portion that is made of a material having good thermal conductivity. The circuit board 6c is fixed to a surface of the heat radiating plate 6d. Therefore, the heat generated by the circuit board 6c is conducted to the heat radiating plate 6d.

According to the present embodiment, the heat radiating plate 6d has another surface opposite the surface thereof to which the circuit board 6c is fixed. The other surface of the radiating plate 6d is exposed in or out of the manipulator body 5 in the vicinity of the display unit rear surface 6b. Consequently, heat conducted to the heat radiating plate 6d is discharged outwardly from the display unit rear surface 6b.

A bending lever 7a, a pointing device 7b, a plurality of switches 7c, and so on are disposed on the manipulator body 5 more closely to the proximal-end side thereof than the display unit 6. The bending lever 7a is used to bend the bendable portion 2b. The pointing device 7b is used to move a cursor and the like displayed on the display 6a. The switches 7c are assigned to various functions of the endoscopic device 1.

As illustrated in FIG. 2, the proximal end side of the manipulator body 5 functions as a light source mount 30 to which the light source unit 4 is detachably attached. The light source mount 30 includes a joined surface 31 positioned below the display unit 6 and extending transversely to the display unit rear surface 6b. As a result, the display unit 6 doubles as a function as a shield that shields an upper surface of a heat radiator 40, to be described hereinafter, of the light source unit 4.

The joined surface 31 has a circular fitting recess 32 defined therein. A light guide 10 has a proximal-end portion projecting from a bottom surface 32b of the recess 32 into the recess 32. On the bottom surface 32b, there are disposed a plurality of terminals, not depicted, to be connected to a board, denoted by 4a in FIG. 4.

The first heat generator may be a board such as the circuit board 6c or the like, whereas the second heat generator may be a light source such as the light source 4L or the like.

The light source unit 4 will be described below with reference to the drawings.

As illustrated in FIG. 2, the light source unit 4 has the heat radiator 40 that can be detachably attached to the light source mount 30 and the light source 4L.

The heat radiator 40 will be described below with reference to FIGS. 3 through 5.

The heat radiator 40 is made of a material having good thermal conductivity, e.g., an aluminum die-casting. As illustrated in FIGS. 3 and 4, the heat radiator 40 is of a substantially L-shaped cross section with a plurality of heat radiating spaces 42 defined therein. The heat radiator 40 includes a joining side plate 43 and a wall 44 that are integrally connected to each other.

The heat radiating spaces 42 are of a predetermined shape each. The heat radiating spaces 42 are defined in the heat radiator 40. In order to define the heat radiating spaces 42 in the heat radiator 40, a plurality of heat radiating members (hereinafter referred to as "fins") 45 are erected from the joining side plate 43. The wall 44 extends from one side of the joining side plate 43 along ends of the fins 45. The wall 44 closes openings of gaps defined between adjacent facing ones of the fins 45 at ends thereof near the joining side plate 43, thereby defining closed spaces in the gaps near the joining side plate 43.

Figure 3:
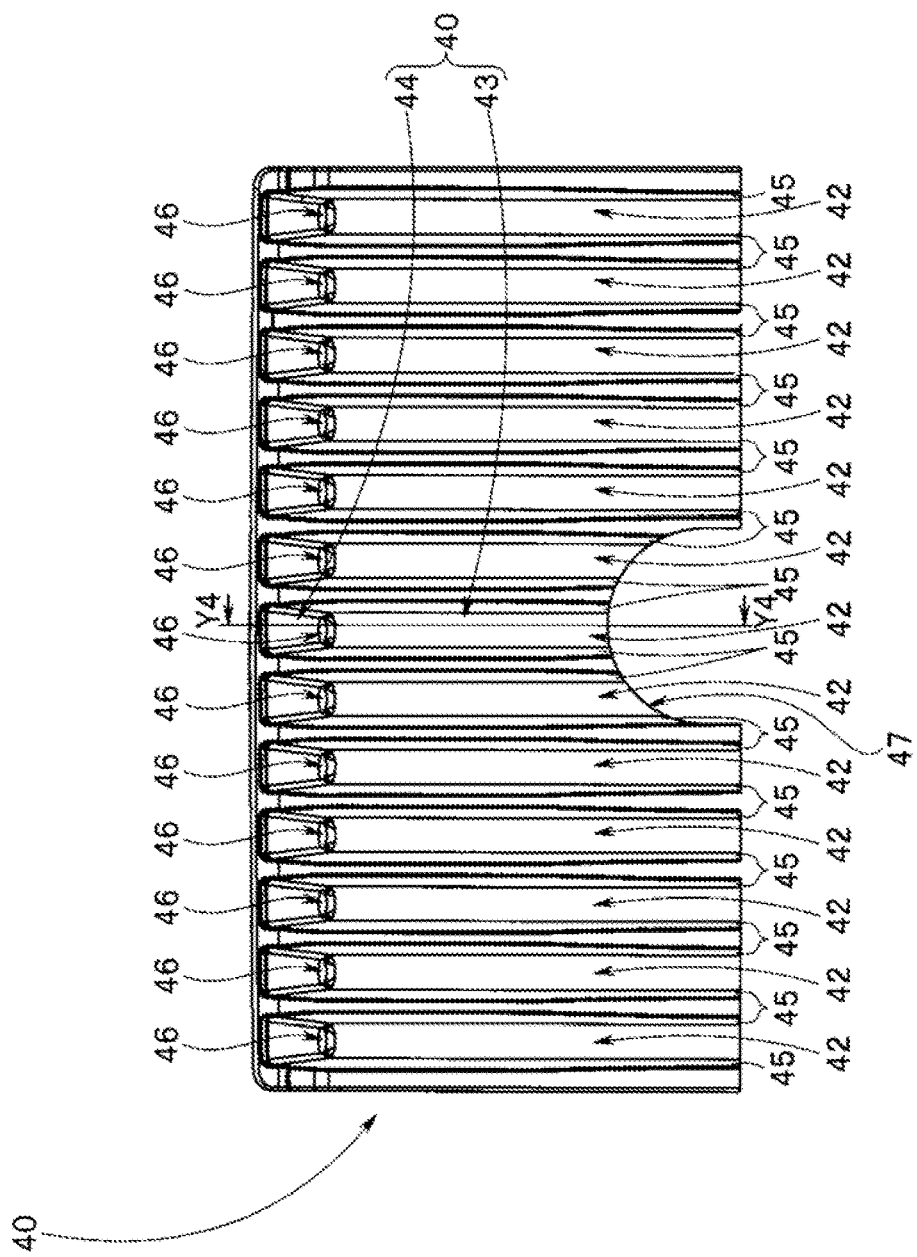
FIG. 3 is a view illustrating a heat radiator having a plurality of heat radiating spaces.
Figure 5:
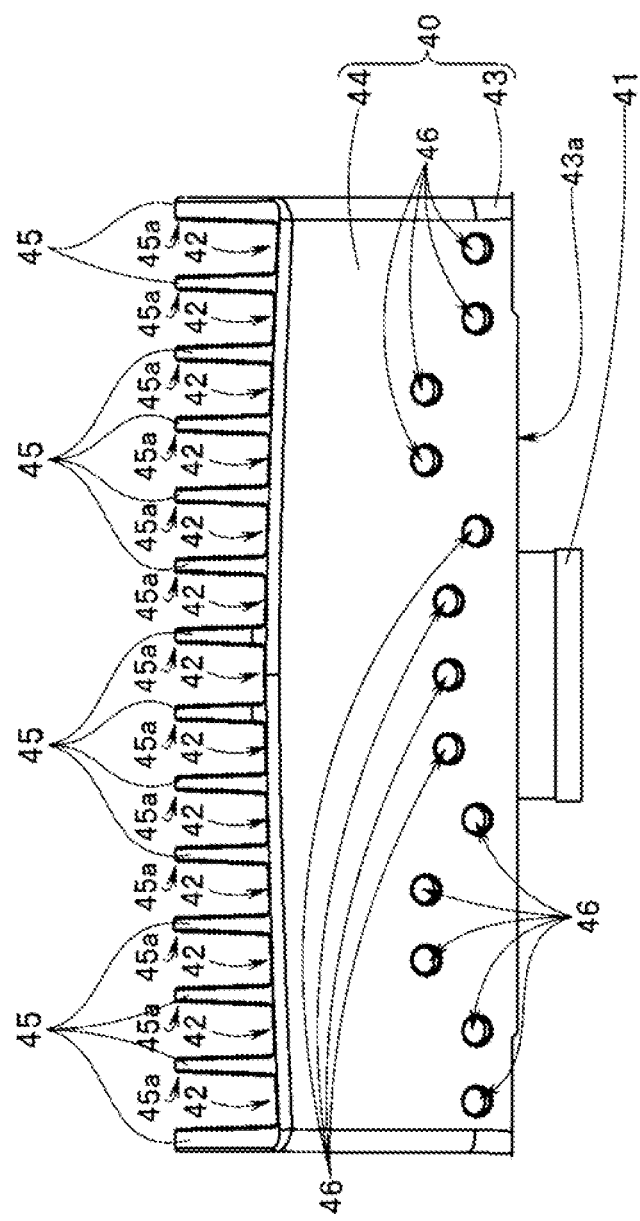
FIG. 5 is a view of the heat radiator as viewed from the arrow Y5 in FIG. 4.

As a consequence, as illustrated in FIGS. 3 and 5, the heat radiating spaces 42 that are closed by the wall 44 are defined as the gaps between the fins 45. According to the present embodiment, the heat radiator 40 functions as a heat sink including the fins 45.

Figure 4:
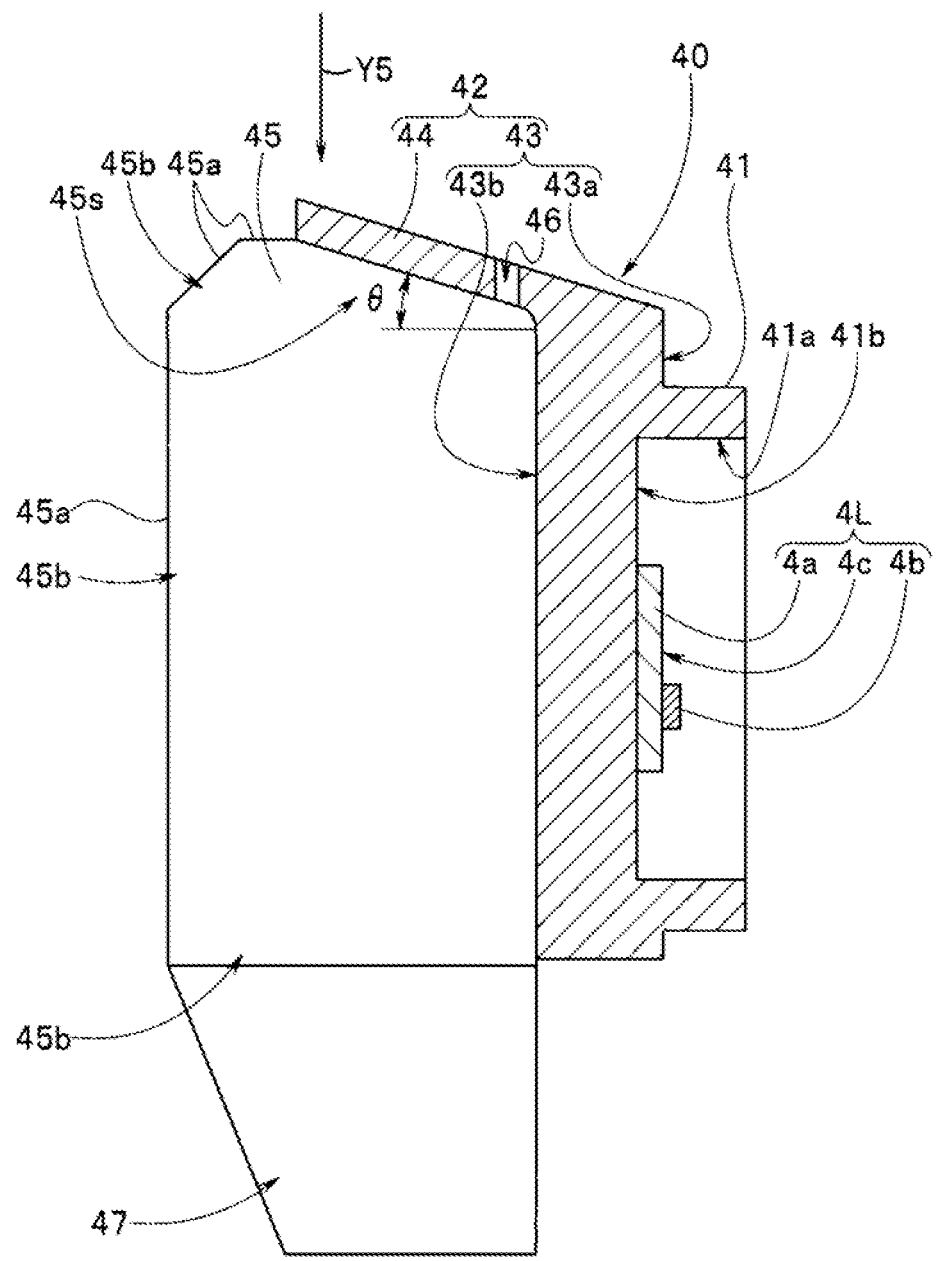
FIG. 4 is a cross-sectional view taken along line Y4-Y4 of FIG. 3.

As illustrated in FIG. 4, the joining side plate 43 has an end surface as a joining surface 43a. The joining side plate 43 also includes an annular flange 41 that protrudes from the joining surface 43a. The light source 4L is disposed in a receptacle 41a defined as a cavity inside the annular flange 41.

The light source 4L mainly includes the board 4a and a light-emitting element 4b such as a light-emitting diode or the like mounted on the board 4a. The board 4a has a mounting surface 4c with interconnects and contacts, not depicted, disposed thereon.

The substrate 4a also has a surface that is opposite the mounting surface 4c and that is thermally connected and fixed to a bottom surface 41b of the receptacle 41a. As a result, the heat generated by the light-emitting element 4b is efficiently conducted to the heat radiator 40.

The joining side plate 43 functions as a heat absorber. The fins 45 are erected from a surface 43b of the joining side plate 43 which is opposite the joining surface 43a, and from an inner surface of the wall 44. The wall 44 is a slanted surface that is inclined at an angle θ to the opposite surface 43b of the joining side plate 43.

As illustrated in FIGS. 3 through 5, the wall 44 has a plurality of vent holes 46 defined therein at predetermined positions near the joining side plate 43. Each of the vent holes 46 is a through hole having a circular opening. The vent holes 46 provide fluid communication between the respective heat radiating spaces 42 and the outside of the heat radiator 40. Therefore, the heat radiating spaces 42 are held in fluid communication with the outside through the vent holes 46 in the wall 44 and open ends 45a on respective end faces of the fins 45.

According to the present embodiment, the number of the vent holes 46 is such that one vent hole 46 is assigned to each heat radiating space 42. However, a plurality of vent holes 46 may be assigned to each heat radiating space 42.

The area of the opening of each of the vent holes 46 is smaller than the area of the open end 45a of each heat radiating space 42. The opening of each of the vent holes 46 is not limited to a circular shape, but may be of an elliptical shape, an elongate round shape, a polygonal shape, or the like.

The heat radiator 40 has a clearance 47 in the form of a U-shaped slot, for example, in which a proximal-end side 2e of the insertion portion 2 is disposed.

In FIGS. 3 through 5, a mounting structure by which the light source unit 4 and the manipulator body 5 are detachably mounted on each other is omitted from illustration.

Operation of the endoscopic device 1 in which the light source unit 4 is integrally mounted on the manipulator body 5 will be described below with reference to FIGS. 6A through 6C.

Figure 6A:
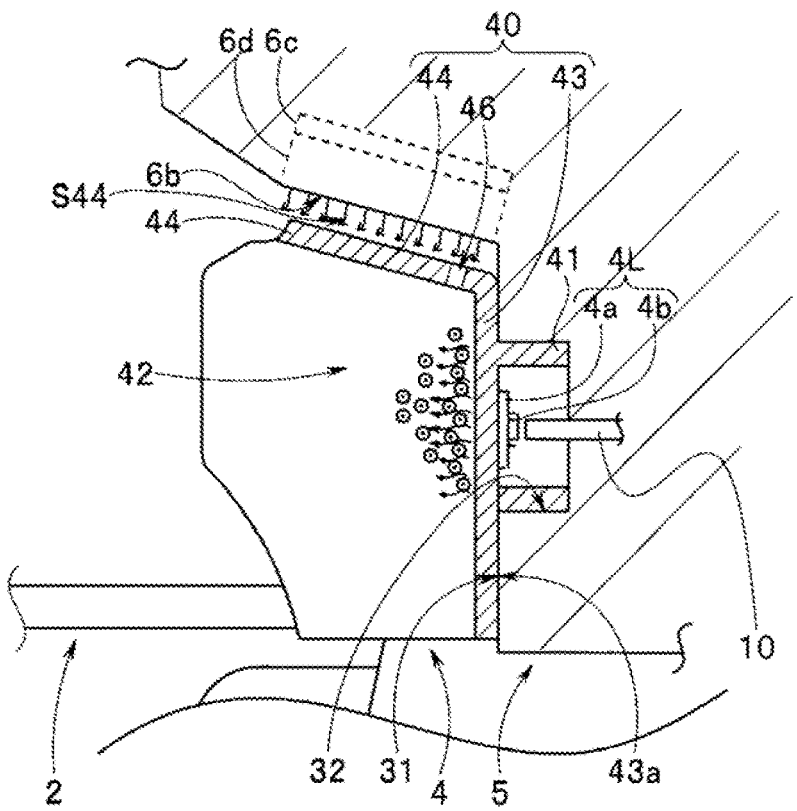
FIG. 6A is a view illustrating the manner in which the endoscopic device operates, with heat being radiated into the heat radiating spaces and a gap.

In preparation for carrying out an endoscopic observation, the user mounts the light source unit 4 integrally on the manipulator body 5, as illustrated in FIG. 6A. At this time, the user places the joining surface 43a against the joined surface 31 such that the wall 44 faces the display unit rear surface 6b of the manipulator body 5.

As a result, a gap S44 is defined between the display unit rear surface 6b and an outer surface of the wall 44. The other surface of the heat radiating plate 6d is disposed within or closely to the gap S44. The vent holes 46 are positioned above the light-emitting element 4b. The openings of the vent holes 46 are disposed in facing relation to the circuit board 6c.

The user turns on the power supply of the endoscopic device 1 to start the observation. The light-emitting element 4b is energized, and the image capturing device, not depicted, is energized. An endoscopic image including ancillary information is displayed on the display 6. As the light-emitting element 4b and the display 6 are energized, the light-emitting element 4b generates heat and the circuit board 6c generates heat.

The heat generated by the light-emitting element 4b is conducted to the joining side plate 43 and then to the fins 45. The heat generated by the circuit board 6c is conducted to the heat radiating plate 6d.

The heat conducted to the joining side plate 43 and the fins 45 is radiated into the heat radiating spaces 42. The heat conducted to the heat radiating plate 6d is radiated into the gap S44.

Figure 6B:
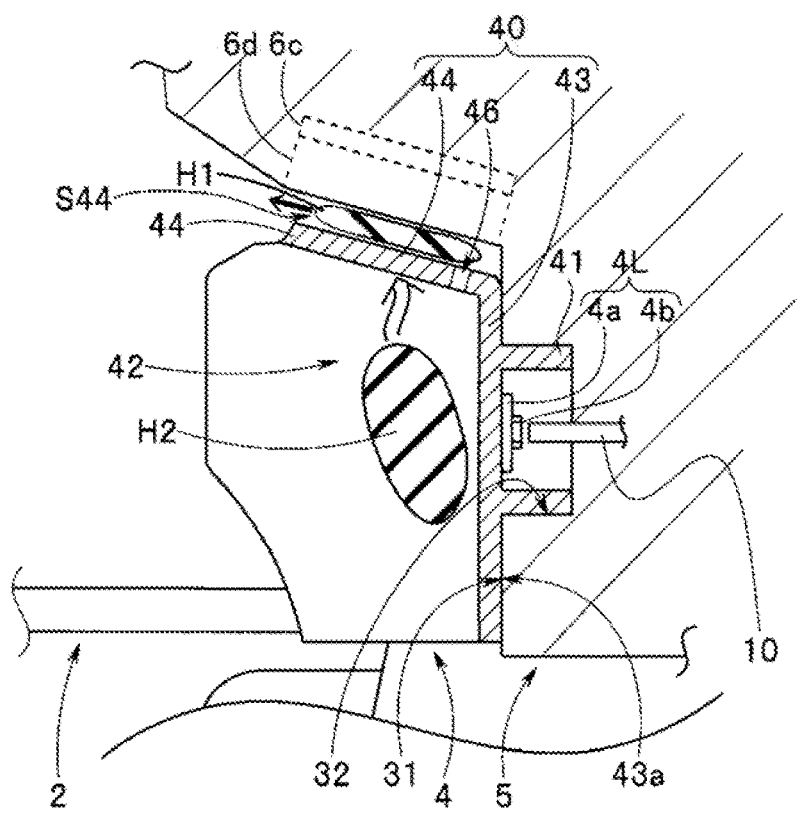
FIG. 6B is a view illustrating high-temperature regions developed in the gap and the heat radiating spaces.

As a consequence, as illustrated in FIG. 6B, a region H1 whose temperature is higher than ambient air temperature is developed in the gap S44. A region H2 whose temperature is higher than ambient air temperature is developed in the heat radiating spaces 42. The gap S44 and the heat radiating spaces 42 are held in fluid communication with each other through the vent holes 46.

Air has its density reduced as its temperature goes higher, and air whose temperature has arisen becomes buoyant. Therefore, air in the gap S44 rises along the slanted outer surface of the wall 44 and moves while drawing in air from the heat radiating spaces 42 through the vent holes 46 into the gap S44. The vent holes 46 now function as an air outlet.

In the heat radiating spaces 42, air whose temperature has arisen rises toward the wall 44 while drawing in air from outside of the heat radiating spaces 42 via the open ends 45a into the heat radiating spaces 42. The open ends 45a now function as an air inlet.

Figure 6C:
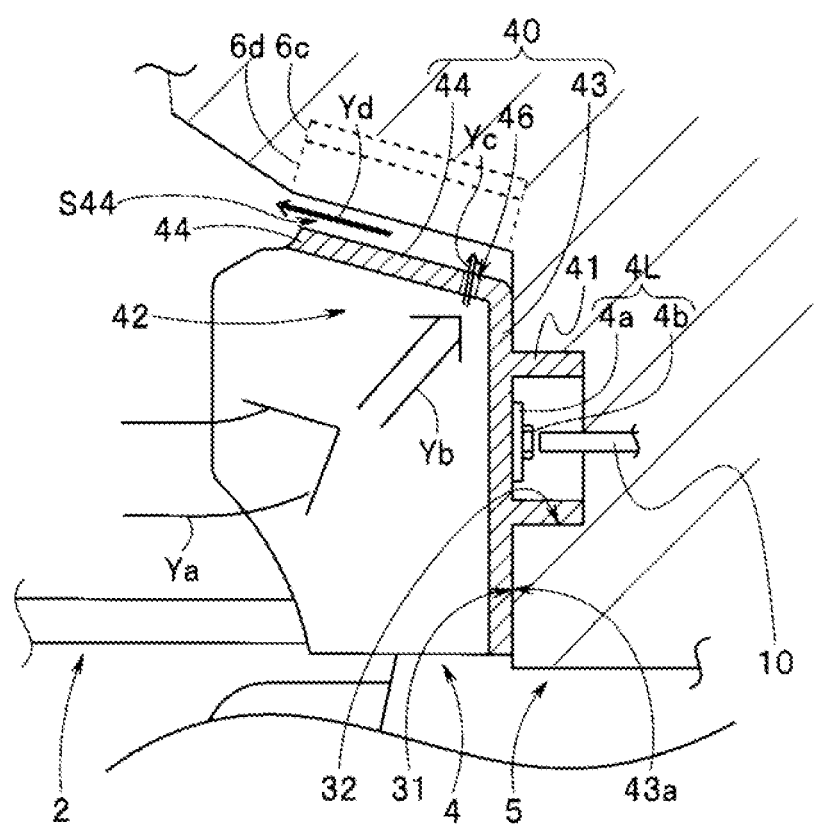
FIG. 6C is a view illustrating the manner in which air warmed by the heat radiated into the heat radiating spaces and the gap is discharged out while drawing in low-temperature external air.

As a result, during the endoscopic observation, as illustrated in FIG. 6C, while drawing in air from outside of the heat radiating spaces 42 via the open ends 45a into the heat radiating spaces 42, i.e., while drawing in air whose temperature is lower than the temperature of air in the heat radiating spaces 42, as indicated by the arrow Ya, heated air in the heat radiating spaces 42 rises and moves toward the vent holes 46, as indicated by the arrow Yb. Thereafter, the rising air flows through the vent holes 46, as indicated by the arrow Yc. Then, the air rises together with the heated air in the gap S44 along the slanted outer surface of the wall 44, and is discharged out of the manipulator 3, as indicated by the arrow Yd.

As described hereinbefore, the vent holes 46 and the open ends 45a are assigned to the heat radiating spaces 42 that are defined by the confronting fins 45 and the wall 44. Air that has risen in temperature in the heat radiating spaces 42 rises in the heat radiating spaces 42 and are discharged from the heat radiating spaces 42 through the vent holes 46 while drawing in ambient air whose temperature is lower than the air in the heat radiating spaces 42 via the open ends 45a, thereby providing a chimney effect for an increased heat radiating capability.

In this manner, the heat radiator 40 is relatively small in size, making the endoscopic device 1 lightweight and allowing the user to carry out satisfactory observations for a long period of time.

Figure 7A:
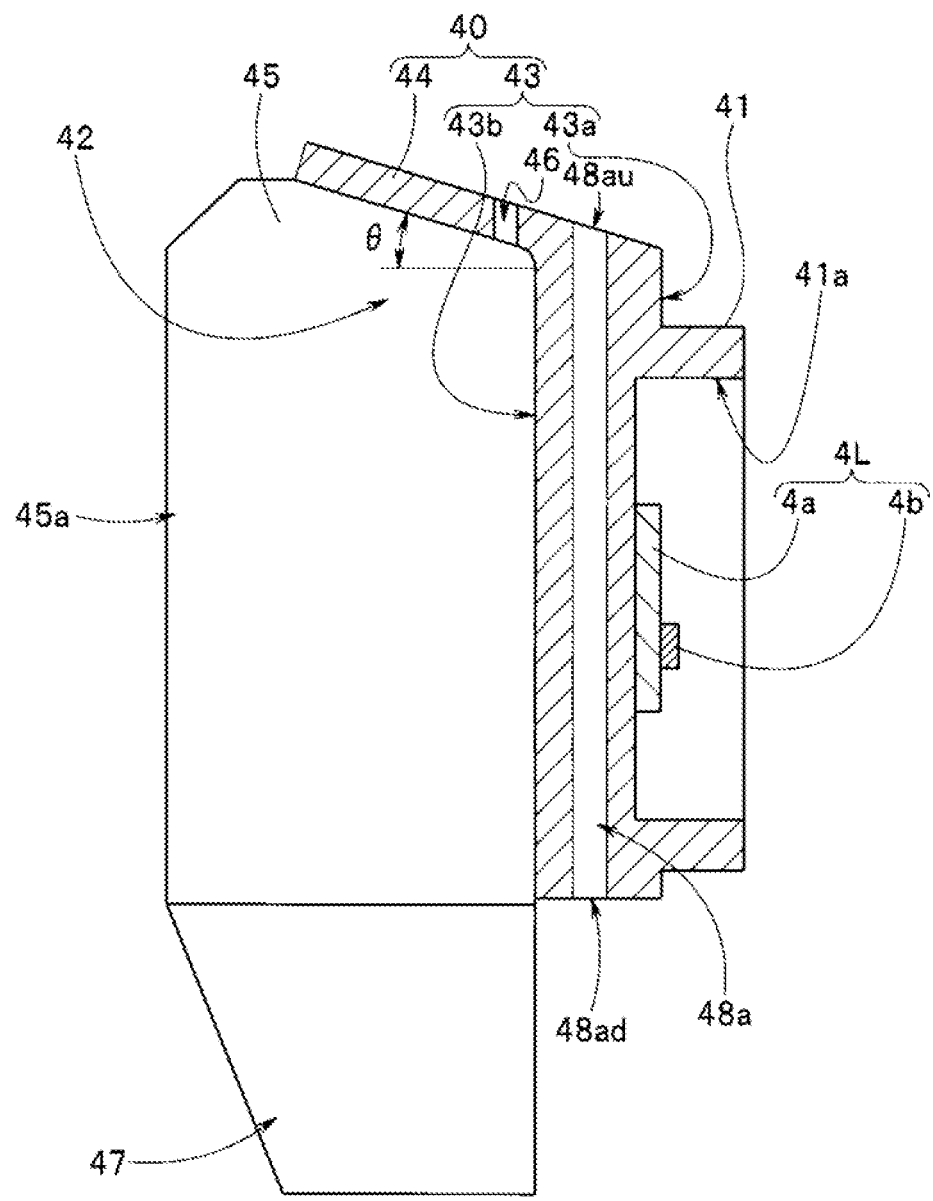
FIG. 7A is a view illustrating a heat radiator with through holes defined in a plate thereof for a chimney effect.

As illustrated in FIG. 7A, the joining side plate 43 of the heat radiator 40 may have a plurality of through holes 48a defined therein that are closer to the light-emitting element 4b than the heat radiating spaces 42. Each of the through holes 48a has an upper-end opening 48au that is open at an upper end thereof near the wall 44 and a lower-end opening 48ad that is open at a lower end thereof near one of the legs 5a remotely from the wall 44.

According to the structure illustrated in FIG. 7A, air in the through holes 48a closer to the light-emitting element 4b is heated earlier than air in the heat radiating spaces 42.

A temperature difference is thus developed in the air in the through holes 48a. As air whose temperature is higher becomes buoyant, the air in the through holes 48a rises in the through holes 48a and is discharged out of the through holes 48a through the upper-end openings 48au while drawing in ambient air through the lower-end openings 48ad into the through holes 48a.

Since the through holes 48a are defined in the joining side plate 43 more closely to the light-emitting element 4b than the heat radiating spaces 42, the through holes 48a develop a chimney effect, discharging the heated air into the gap S44 for smooth heat radiation.

Figure 7B:
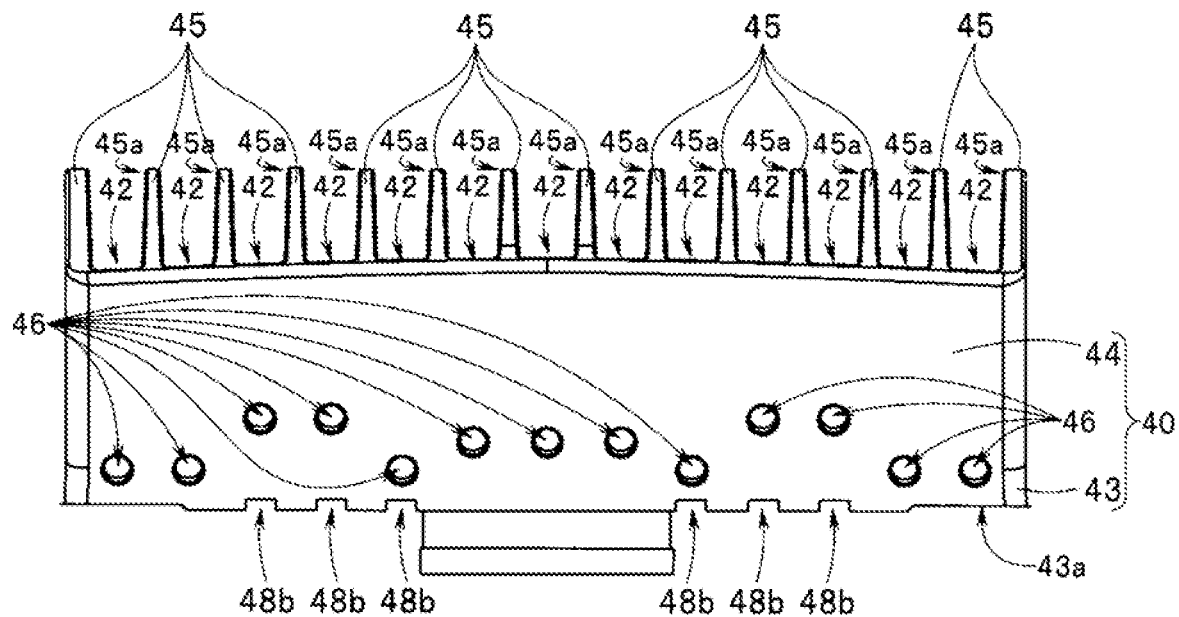
FIG. 7B is a view illustrating a heat radiator with grooves defined in a plate thereof which will be converted into through holes for a chimney effect.

In FIG. 7A, the through holes (also referred to as "chimney holes") 48a are defined in the joining side plate 43 more closely to the light-emitting element 4b than the heat radiating spaces 42. However, as illustrated in FIG. 7B, the joining side plate 43 may have a plurality of grooves 48b that are defined in the joining surface 43a thereof and that have openings at the joining surface 43a.

Figure 7C:
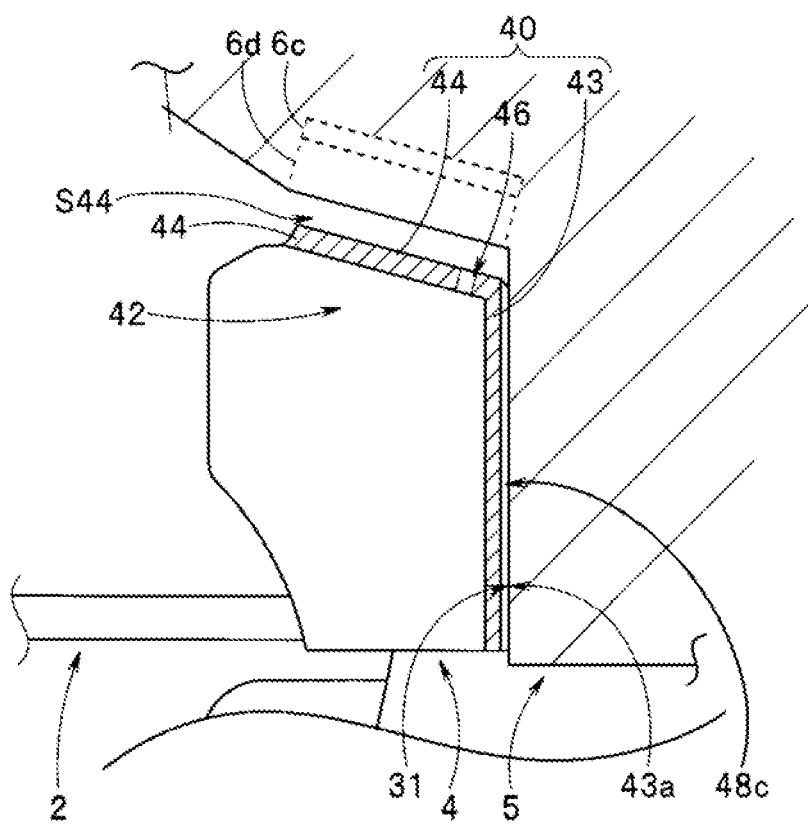
FIG. 7C is a view illustrating the through holes that have been converted from the grooves by placing a joining surface against a joined surface.

When the joining surface 43a is placed against the joined surface 31, the openings of the grooves 48b are closed by the joined surface 31. Therefore, the grooves 48b are converted into chimney holes 48c, as illustrated in FIG. 7C.

As a result, the chimney holes 48c may be positioned more closely to the light-emitting element 4b. The chimney holes 48c thus positioned are able to develop a chimney effect more quickly than in the embodiment described hereinbefore, discharging heated air into the gap S44 for efficient heat radiation.

Figure 7D:
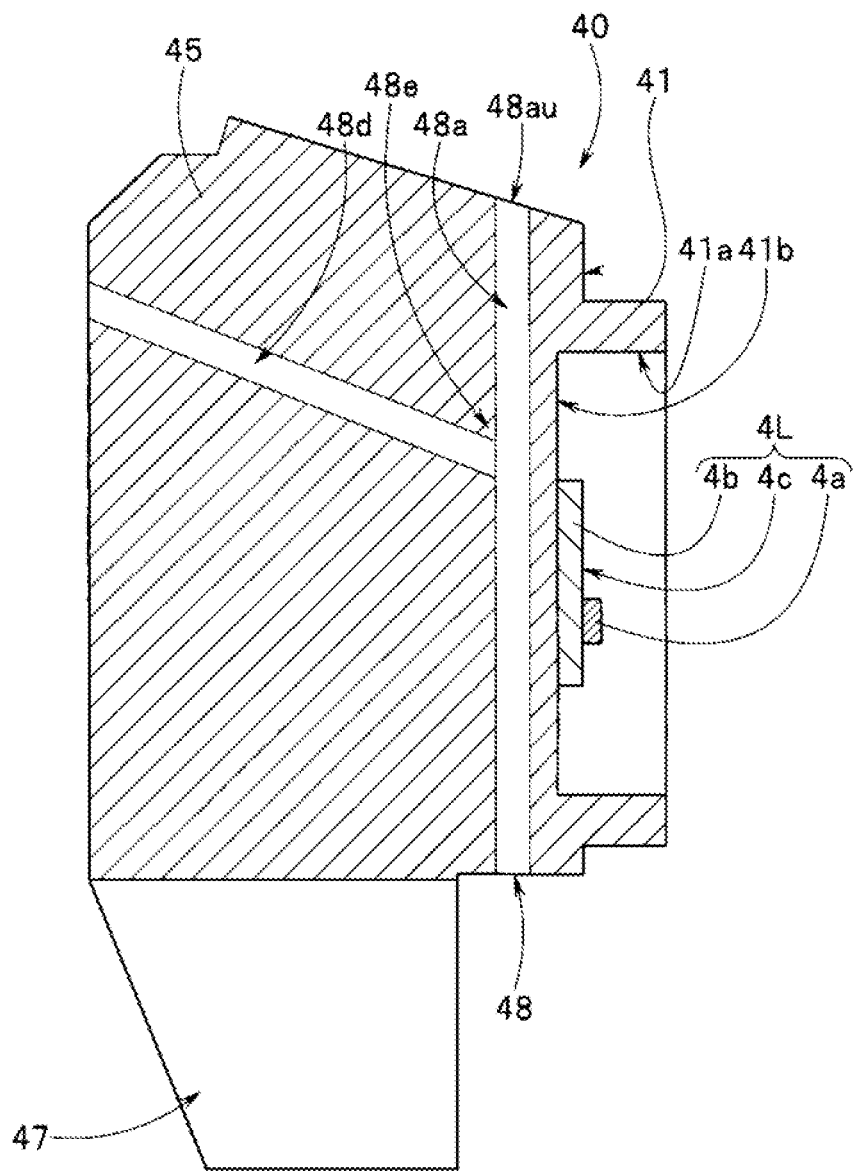
FIG. 7D is a view illustrating inclined holes defined in a plate and heat radiating members transversely to intermediate portions of through holes defined in the plate.

The chimney holes 48a and 48c may be positioned in alignment with the fins 45, and, as illustrated in FIG. 7D, inclined holes 48d may be defined in the fins 45 and the joining side plate 43 transversely to intermediate portions of through holes 48a and 48c, for example.

The inclined holes 48d have ends joined to the chimney holes 48a in respective intersecting regions 48e that are positioned more closely to the wall 44 than the light-emitting element 4b, i.e., above the light-emitting element 4b. The other ends of the inclined holes 48a are open at the open ends of the fins 45.

According to the structure illustrated in FIG. 7D, the chimney holes 48a develop a chimney effect to cause heated air to rise the chimney holes 48a while drawing in ambient air through the lower-end openings 48 into the chimney holes 48a. At this time, the rising air is divided at the intersecting regions 48e into the chimney holes 48a and the inclined holes 48d before it is discharged from the heat radiator 40.

Since the divided heated air moves through the inclined holes 48d and is then discharged therefrom, the air in the heat radiating spaces 42 above the light-emitting element 4b is heated by the air flowing through the inclined holes 48d. Therefore, the inclined holes 48d also develop a chimney effect to accelerate heat radiation.

Although not illustrated, the inclined holes 48d may be joined to intermediate portions of the grooves 48b (see FIG. 7B) transversely thereto.

In the embodiment described hereinbefore, when the joining surface 43a is placed against the joined surface 31, the gap S44 is defined between the display unit rear surface 6b and the outer surface of the wall 44.

Figure 8:
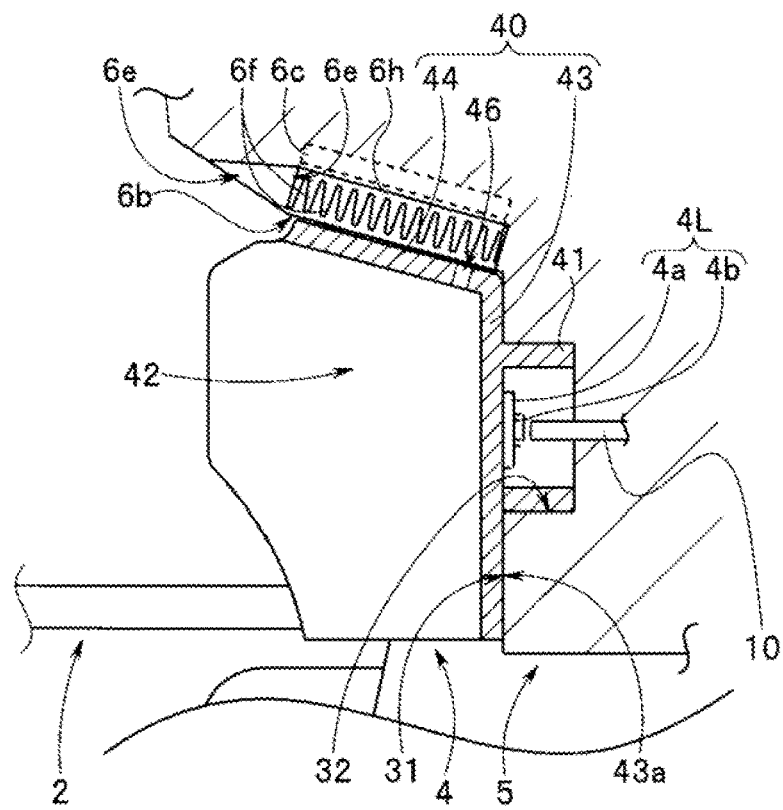
FIG. 8 is a view illustrating a manipulator body having a recess defined therein that has an opening at a display unit rear surface.

However, as illustrated in FIG. 8, a recess 6e such as a groove, a hole, or the like may be defined in the display unit rear surface 6b and may be open at the display unit rear surface 6b. The other surface of the heat radiating plate 6d may be disposed in the recess 6e.

According to the structure illustrated in FIG. 8, if the heat radiating plate 6d functions as a heat sink 6h having fins 6f on the other surface thereof, then the fins 6f that are disposed in the recess 6e are prevented from damage. The heat generated by the circuit board 6c is efficiently discharged through the heat sink 6h into the recess 6e.

Heated air discharged into the recess 6e rises along the inclined upper surface of the wall 44 and is then discharged out of the manipulator 3.

According to the embodiment described hereinbefore, the display unit 6 doubles as a shield. However, if an endoscopic device includes a display device, not depicted, as an external device separate from the manipulator 3, then, as illustrated in FIG. 9, the manipulator 3 has a manipulator body 5B including a dedicated shield 5c.

The shield 5c has a slanted surface 5d facing the wall 44 and a recess 5e that is defined in the slanted surface 5d and that is open at the slanted surface 5d. The recess 5e has a predetermined depth. The recess 5e has a proximal end that may be open as indicated by the broken line or that may be closed as indicated by the solid line.

The manipulator body 5B has other structural details essentially similar to those of the manipulator body 5. Those parts of the manipulator body 5B that are identical to those of the manipulator body 5 are denoted by identical reference characters and will not be described in detail below.

Figure 9:
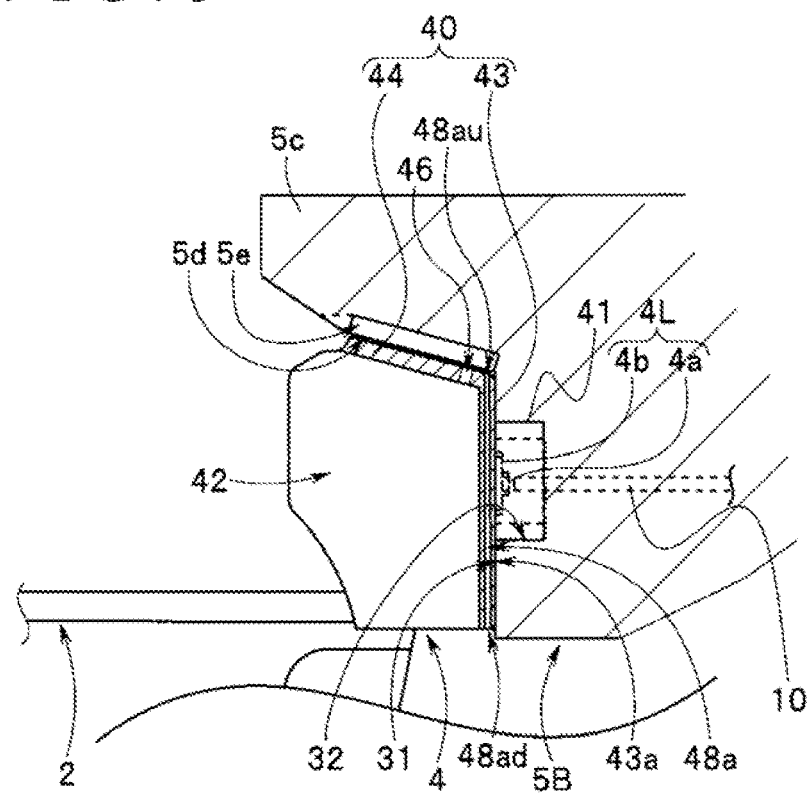
FIG. 9 is a view illustrating the relationship between a manipulator body having a dedicated shield and a light source unit.

In the structure illustrated in FIG. 9, the heat radiator 40 has a plurality of chimney holes 48a defined in the joining side plate 43 as with the structure illustrated in FIG. 7A.

According to the structure illustrated in FIG. 9, while the user carries out an observation with the light source unit 4 being integrally mounted on the manipulator body 5B, the heat generated by the light-emitting element 4b is conducted to the joining side plate 43 and then to the fins 45.

Inasmuch as air in the chimney hole 48a is close to the light-emitting element 4b, it is heated earlier than air in the heat radiating spaces 42. A temperature difference is thus developed in the air in the chimney holes 48a. The chimney holes 48a develop a chimney effect, supplying the heated air discharged from the upper-end openings 48au to the recess 5e.

The recess 5e functions in the same manner as the gap S44. In other words, in the absence of the circuit board 6c, a region whose temperature is higher than ambient air temperature is produced in the recess 5e by the air discharged from the upper-end openings 48au into the recess 5e.

The air in the recess 5e rises along the slanted outer surface of the wall 44 and moves while drawing in air from the heat radiating spaces 42 through the vent holes 46 into the recess 5e.

In the heat radiating spaces 42, a region whose temperature is higher than ambient air temperature is produced by the heat radiated from the fins 45. The air in the region rises toward the wall 44 while drawing in ambient air from the open ends 45a into the heat radiating spaces 42.

As a consequence, the structure illustrated in FIG. 9 operates and offers effects in the same manner as the embodiment described hereinbefore.

In the embodiment described hereinbefore, the light source unit 4 includes the heat radiator 40 and the light source 4L combined therewith. However, the heat radiator may be an independent heat radiator.

FIG. 10A illustrates an endoscopic device 3A having a heat radiator 40A and manipulator body 50. Unlike the heat radiator 40 according to the embodiment described hereinbefore, the heat radiator 40A has a joining surface 43a as a proximal-end surface that is free of the annular flange 41. Other structural details of the heat radiator 40A are similar to those of the heat radiator 40 according to the embodiment described hereinbefore.

The manipulator body 50 includes a light source 60 (see FIG. 10B) integrally fixed thereto.

Figure 10B:
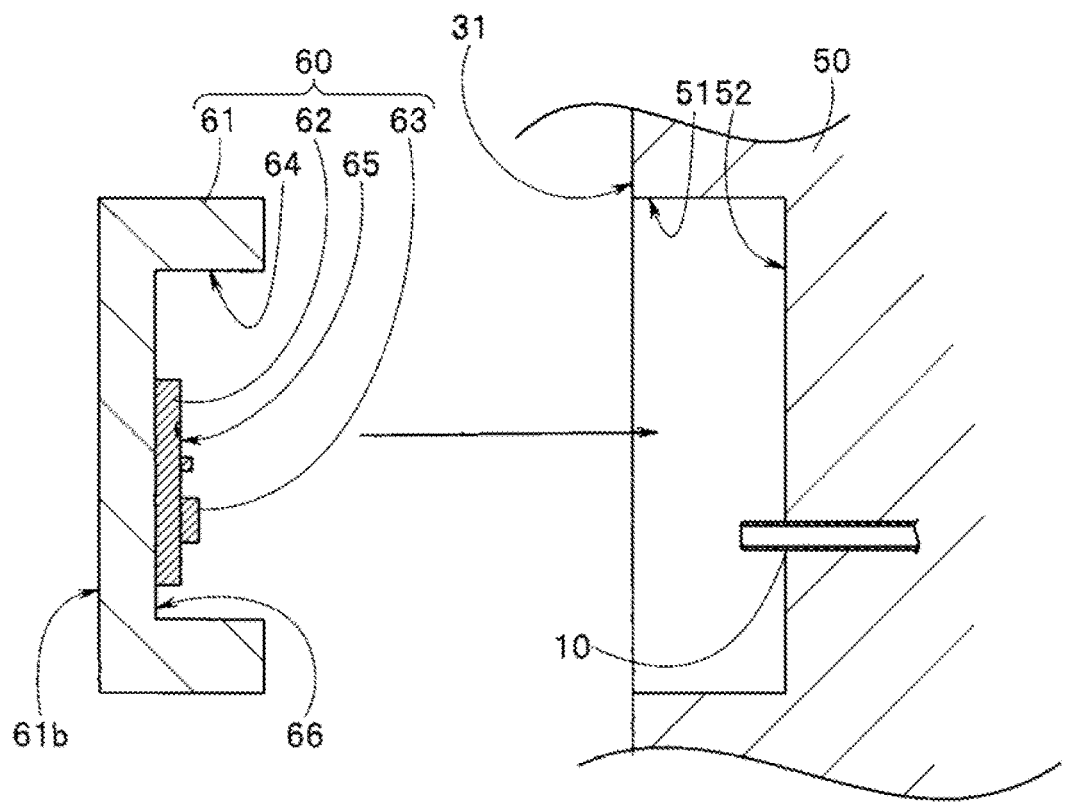
FIG. 10B is a view illustrating the relationship between the light source and the manipulator body.

As illustrated in FIG. 10B, the light source 60 includes a frame 61, a board 62, and a light-emitting element 63. The frame 61 is of a hollow cylindrical shape with a recess 64 defined therein. The light-emitting element 63 is mounted on the board 62. The board 62 has a mounting surface 65 with interconnects and contacts, not depicted, disposed thereon. The board 62 has another surface that is opposite to the mounting surface 65 and that is thermally connected and fixed to a bottom surface 66 of the frame 61. The frame 61 has a rear surface 61b opposite to the bottom surface 66.

The manipulator body 50 has a circular fitting recess 51 defined therein. The fitting recess 51 functions as a receptacle in which the light source 60 is disposed. A light guide 10 has a proximal-end portion projecting from a bottom surface 52 of the recess 51 into the recess 51. On the bottom surface 52, there are disposed a plurality of terminals, not depicted, to be connected to contacts, etc. on the board 62 of the light source 60.

The manipulator body 50 illustrated in FIG. 10A is assembled when the frame 61 of the light source 60 is placed in the fitting recess 51 in the manipulator body 50.

Figure 10C:
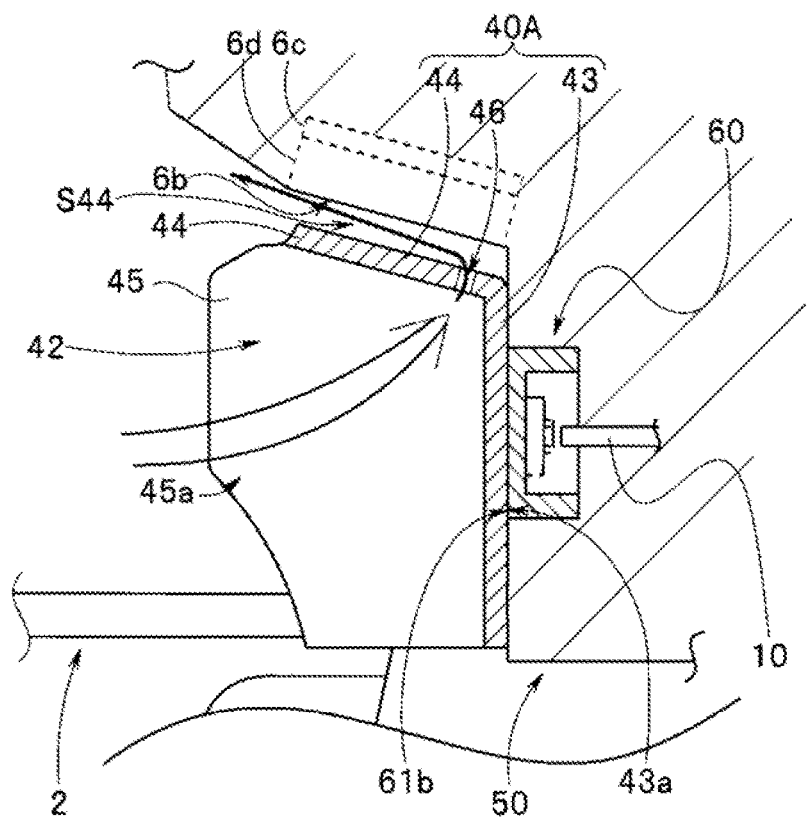
FIG. 10C is a view illustrating the manner in which the endoscopic device illustrated in FIG. 10A operates, with heat being radiated.

In preparation for carrying out an endoscopic observation, the user mounts the heat radiator 40A integrally on the manipulator body 50 by joining the joining surface 43a on the rear surface 61b of the frame 61, as illustrated in FIG. 10C.

As a result, a gap S44 is defined between the display unit rear surface 6b and an outer surface of the wall 44, as described hereinbefore. The other surface of the heat radiating plate 6d is disposed within or closely to the gap S44. The vent holes 46 are positioned above the light-emitting element 4b.

According to the present embodiment, the heat generated by the light-emitting element 4b is conducted from the rear surface 61b of the frame 61 through the joining surface 43a to the joining side plate 43 and then to the fins 45.

As described hereinbefore, the heat conducted to the joining side plate 43 and the fins 45 is radiated into the heat radiating spaces 42. The heat conducted to the heat radiating plate 6d is radiated into the gap S44.

Consequently, as described hereinbefore, as illustrated in FIG. 6C, while drawing in air from outside of the heat radiating spaces 42 via the open ends 45a into the heat radiating spaces 42, heated air in the heat radiating spaces 42 rises and moves toward the vent holes 46. Thereafter, the rising air flows through the vent holes 46. Then, the air rises together with the heated air in the gap S44 along the slanted outer surface of the wall 44, and is discharged out of the manipulator 3.

Thus, the heat radiator 40A also develops a chimney effect for an increased heat radiating capability.

In sum, one aspect of the disclosed technology is directed to an endoscopic device comprises a manipulator body. An insertion portion includes opposed respective proximal and distal ends. The insertion portion is connected to the manipulator body via the proximal end. A first heat generator is configured to be attached to the manipulator body. A heat radiator is configured to be detachably attached to the manipulator body and is thermally connected to the first heat generator. The heat radiator includes at least one air inlet port through which air flows in and at least one air outlet port having an area smaller than an area of the at least one air inlet port.

The at least one air inlet port is located in a lower elevation with respect to the at least one air outlet port so as to form pressure differential for air circulation. The at least one air outlet port includes a through hole located for discharging the heat generated by the first heat generator and directed to the heat radiator in a predetermined direction in the manipulator body. A second heat generator is configured to be attached to the manipulator body. A second heat radiator on which the second heat generator is mounted, the second heat radiator is disposed outside of the manipulator body and is thermally connected to the second heat generator. The at least one air outlet port includes a through hole located for discharging the heat generated by the first heat generator and directed to the heat radiator in a direction toward the second heat radiator. The at least one air outlet port is located in higher elevation with respect to the first heat generator. A second heat generator is configured to be attached to the manipulator body. A second heat radiator is disposed outside of the manipulator body and thermally connected to the second heat generator. The at least one air outlet port is located in facing relation to the second heat radiator. The at least one air outlet port provides fluid communication between a space and a gap. The space is formed in the heat radiator that discharges the heat generated from the first heat generator. The gap is formed between the manipulator body and the heat radiator. The heat generated from the second heat generator is discharged into the gap. The first heat generator is defined by a light source and the light source and the heat radiator in combination form a light source unit that detachably mounted on the manipulator body. The heat radiator has a plurality of heat radiating members. A plate on which the heat radiating members are erected, and a wall closing portions of gaps defined between facing ones of the heat radiating members making the gaps into heat radiating spaces. The at least one air inlet port includes open ends on respective end faces of the heat radiating members which face each other across the heat radiating spaces. The at least one air outlet port is defined in the wall and held in fluid communication with the heat radiating spaces. The first heat generator is defined by a light source unit having a light source. The second heat generator is defined by an electronic board. The plate has a plurality of through holes defined therein and having openings that are open in a surface thereof near the wall and other openings that open in a surface thereof remote from the wall. The plate has a plurality of grooves that are defined in a joining surface thereof. The plate and the manipulator body forms through holes at the plurality of the grooves when the plurality of the grooves are closed by the manipulator body. The plate and the heat radiating members have inclined holes defined therein and joined to intermediate portions of the through holes. The inclined holes are joined to the through holes in respective intersecting regions that are positioned above the first heat generator.

Another aspect of the disclosed technology is directed to a heat radiator constructed within an endoscope that comprises a plurality of heat radiating members spaced apart from one another. A plurality of air inlet ports which are located respectively in the heat radiating members and through which air flows in and an air outlet port having an area smaller than each of the plurality of air inlet ports and through which air flows out of the heat radiating members. The plurality of air inlet ports is located in lower elevation with respect to the air outlet port.

A plate on which the heat radiating members are erected and a wall closing portions of gaps defined between facing ones of the heat radiating members making the gaps into the heat radiating spaces. The plurality of air inlet ports includes open ends on respective end faces of the heat radiating members which face each other. The air outlet includes at least one air outlet defined in the wall that defines the heat radiating spaces.

A further aspect of the disclosed technology is directed to an endoscope device comprises a manipulator body and an insertion portion having opposed respective proximal and distal ends. The insertion portion is connected to the manipulator body via the proximal end. A light source unit is configured to be detachably attached to the manipulator body. The light source unit includes a heat radiator used to dissipate heat produced by the light source unit during an operation of the endoscope device. The heat radiator includes one or more air passages formed in specific locations so as to define a chimney when dissipating the heat away from the endoscope device.

An embodiment is an endoscope device comprising a manipulator body; an insertion portion having opposed respective proximal and distal ends wherein the insertion portion is connected to the manipulator body via the proximal end; a light source unit configured to be detachably attached to the manipulator body, the light source unit includes a heat radiator used to dissipate heat produced by the light source unit during an operation of the endoscope device wherein the heat radiator includes one or more air passages formed in specific locations so as to define a chimney when dissipating the heat away from the endoscope device.

A first variation of the embodiment is where the manipulator body is defined by an elongated body having a plurality of buttons and/or switches that are used to control bending operation of the insertion portion.

A second variation of the embodiment is where the manipulator body includes a display unit having a video processing circuit board to electronically communicate with the insertion portion.

The second variation of the embodiment can be further modified such that the video processing circuit board produces heat during the operation which the heat is dissipated away from the endoscope device by the heat radiator.

A third variation of the embodiment is where the heat radiator includes a wall having a plurality vent holes formed therein and a joining side plate that are integrally attached to one another.

A fourth variation of the embodiment is where the heat radiator includes a plurality of heat radiating members that are erected outwardly from the joining side plate.

The third variation of the embodiment can be further modified such that the joining side plate is used as a heat absorber.

The third variation of the embodiment can be further yet modified such that the joining side plate includes an annular flange that protrudes therefrom, the annular flange includes a receptacle that is used to receive the light source unit.

The fourth variation of the embodiment can be further modified such that the plurality of heat radiating members and the plurality of vent holes configuration on the wall provide a chimney effect when the endoscope device is in the operation.

The fourth variation of the embodiment can be further yet modified such that the manipulator body includes a plurality of legs extending outwardly so as to provide a space for air circulation that enhances heat dissipation from the endoscope device.

A further embodiment is an endoscope device comprising an endoscope having a plurality of heat producing units configured to be used to conduct a visual inspection, the endoscope includes a heat radiator used to dissipate heat produced by the plurality of heat producing units during an operation of the endoscope device wherein the heat radiator includes one or more air passages formed in specific locations for providing an effective air circulation via a chimney effect when dissipating the heat away from the endoscope device.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscopic device comprising:
   a manipulator body;
   an insertion portion having opposed respective proximal and distal ends wherein the insertion portion is connected to the manipulator body via the proximal end;
   a first heat generator configured to be attached to the manipulator body; and
   a heat radiator configured to be detachably attached to the manipulator body and thermally connected to the first heat generator, wherein
   the heat radiator includes at least one air inlet port through which air flows in and at least one air outlet port having an area smaller than an area of the at least one air inlet port.

2. The endoscopic device of claim 1, wherein the at least one air inlet port is located in a lower elevation with respect to the at least one air outlet port so as to form pressure differential for air circulation.

3. The endoscopic device of claim 2, wherein the at least one air outlet port is located in higher elevation with respect to the first heat generator.

4. The endoscopic device of claim 3, wherein the heat radiator is a first heat radiator and the endoscopic device further comprising
   a second heat generator configured to be attached to the manipulator body; and
   a second heat radiator disposed outside of the manipulator body and thermally connected to the second heat generator, wherein
   the at least one air outlet port is located in facing relation to the second heat radiator.

5. The endoscopic device of claim 1, wherein the at least one air outlet port includes a through hole located for discharging the heat generated by the first heat generator and directed to the heat radiator in a predetermined direction in the manipulator body.

6. The endoscopic device of claim 1, wherein the heat radiator is a first heat radiator and the endoscopic device further comprising:
   a second heat generator configured to be attached to the manipulator body; and
   a second heat radiator on which the second heat generator is mounted, the second heat radiator being disposed outside of the manipulator body and thermally connected to the second heat generator, wherein
   the at least one air outlet port includes a through hole located for discharging the heat generated by the first heat generator and directed to the heat radiator in a direction toward the second heat radiator.

7. The endoscopic device of claim 6, wherein the at least one air outlet port provides fluid communication between a space and a gap, the space being formed in the first heat radiator that discharges the heat generated from the first heat generator, the gap being formed between the manipulator body and the first heat radiator, the heat generated from the second heat generator being discharged into the gap.

8. The endoscopic device of claim 6, wherein the second heat generator is defined by an electronic board.

9. The endoscopic device of claim 1, wherein
   the first heat generator being defined by a light source; and
   the light source and the heat radiator in combination form a light source unit that detachably mounted on the manipulator body.

10. The endoscopic device of claim 1, wherein
    the heat radiator has a plurality of heat radiating members, a plate on which the heat radiating members are erected, and a wall closing portions of gaps defined between facing ones of the heat radiating members, making the gaps into heat radiating spaces; and
    the at least one air inlet port includes open ends on respective end faces of the heat radiating members which face each other across the heat radiating spaces.

11. The endoscopic device of claim 10, wherein the at least one air outlet port is defined in the wall and held in fluid communication with the heat radiating spaces.

12. The endoscopic device of claim 10, wherein the plate has a plurality of through holes defined therein and having openings that are open in a surface thereof near the wall and other openings that open in a surface thereof remote from the wall.

13. The endoscopic device of claim 12, wherein the plate and the heat radiating members have inclined holes defined therein and joined to intermediate portions of the through holes.

14. The endoscopic device of claim 13, wherein the inclined holes are joined to the through holes in respective intersecting regions that are positioned above the first heat generator.

15. The endoscopic device of claim 10, wherein
the plate has a plurality of grooves that are defined in a joining surface thereof and wherein
the plate and the manipulator body forms through holes at the plurality of the grooves when the plurality of the grooves are closed by the manipulator body.

16. The endoscopic device of claim 1, wherein the first heat generator is defined by a light source unit having a light source.

17. An endoscope device comprising:
a manipulator body;
an insertion portion having opposed respective proximal and distal ends wherein the insertion portion is connected to the manipulator body via the proximal end;
a light source unit configured to be detachably attached to the manipulator body, the light source unit includes a heat radiator used to dissipate heat produced by the light source unit during an operation of the endoscope device wherein the heat radiator includes one or more air passages configured to dissipate the heat away from the endoscope device.

* * * * *